United States Patent [19]

Doran et al.

[11] 4,352,821

[45] Oct. 5, 1982

[54] SWEET TABLETING AGENT

[75] Inventors: Mark A. Doran, Sunnyvale; Thomas R. Rumolo, Fremont, both of Calif.

[73] Assignee: Shaklee Corporation, Emeryville, Calif.

[21] Appl. No.: 285,639

[22] Filed: Jul. 21, 1981

[51] Int. Cl.$^3$ .................. A61K 31/70; A61K 9/16; A61K 9/20
[52] U.S. Cl. .................................................. 424/361
[58] Field of Search ............................. 424/361, 362

[56] References Cited

U.S. PATENT DOCUMENTS

| 3,639,169 | 2/1972 | Broeg et al. | 424/362 |
| 3,907,204 | 10/1976 | Monti | 424/361 |
| 4,007,052 | 2/1977 | Heinemann et al. | 127/30 |
| 4,013,775 | 3/1977 | Nelson et al. | 426/285 |

FOREIGN PATENT DOCUMENTS 2519714 11/1976 Fed. Rep. of Germany.

*Primary Examiner*—Shep K. Rose
*Attorney, Agent, or Firm*—Majestic, Gallagher, Parsons & Siebert

[57] ABSTRACT

A composition, useful as a sweet tableting agent in tablet formulations, comprises a compressible granule. The compressible granule is formed from fructose and a carrier for the fructose. The carrier is preferably an edible, substantially water insoluble inorganic salt. A preferred compressible granule has about 20 to about 55 wt. % fructose and a moisture content of less than about 2 wt. %.

15 Claims, 6 Drawing Figures

SWEET TABLETING AGENT

TECHNICAL FIELD

The present invention relates generally to direct compression vehicles for use in tableting, and more particularly to a compressible sweet tableting agent which includes fructose.

BACKGROUND ART

Tablets are popular and useful for providing active ingredients such as pharmaceuticals, vitamins, and minerals in a solid dosage form. Tablets possess various advantages over other solid dosage forms. For example, the active ingredients in tablets are frequently more stable than in granules and powders, and tablets provide uniformity in composition, convenience of administration, and may be produced quickly in high volume.

Direct compression in a tableting press is a preferred method of producing tablets. This requires using ingredients which have the necessary properties of flowability and compressibility. Few materials, by themselves, have these properties to a sufficient degree so as to be tableted in a tableting press.

Flowability is the property of the ingredients to be transported uniformly during production, such as from storage bins to hoppers and ultimately to the tablet die of the tableting press. Once the die is uniformly filled, the ingredients must be compressible. In order to be compressible for the purposes of tableting, the ingredient must form a stable compact, or tablet, when sufficient pressure is applied by a set of tablet punches of the tableting press. Direct compression vehicles, or tableting agents, are commercially available which possess sufficient flowability and compressibility properties so that when quantities of other ingredients, such as pharmaceuticals, vitamins, and minerals, are admixed therewith, then the admixture can be directly compressed on a tableting press.

Among the commercially available direct compression vehicles are sorbitol, mannitol, sucrose (sold by Amstar as Di Pac), corn syrup solids (sold by E. M. Mendell Co. as Emdex), microcrystalline cellulose, and dicalcium phosphate dihydrate. Several of these commercially available vehicles are sweet tasting and thus provide a pleasant taste, if the tablet is chewed, as well as function as a tableting agent when the tablet is prepared.

Although several of the commercially available direct compression vehicles are monosaccharides, the monosaccharide fructose has not previously been suitable as a direct compression vehicle. This is apparently due to the nature of pure anhydrous crystalline fructose, whose normal crystal configuration does not lend itself to direct compression in a tableting press. Nevertheless, fructose has found wide acceptance as a raw material, especially in the food supplement area, for its sweetness and solubility in aqueous solutions. Where commercially available fructose has been admixed in tablet formulations as an ingredient, auxiliary binders, including at least one direct compression vehicle, must be incorporated in the admixture if a direct compression process is desired.

Among the auxiliary binders, or excipients, used widely in the pharmaceutical and food supplement industry are tricalcium phosphate, dicalcium phosphate anhydrous, and magnesium carbonate. These excipients are used as mineral sources or for functions such as glidants. However, these excipients are normally present in tablets as low percentages, and do not, by themselves, function as direct compression vehicles.

DISCLOSURE OF THE INVENTION

It is an object of the present invention to provide a composition including fructose which is directly compressible and is useful as a tableting agent.

It is another object of the present invention to provide a sweet tableting agent whose excellent compressibility minimizes the amount necessary for admixture with other ingredients, but which forms tablets having at least comparable compressibility to prior known tableting formulations.

In one aspect of this invention, a composition comprises fructose and a substantially water insoluble carrier for the fructose. The fructose and the carrier together form a compressible granule. The fructose is in a weight ratio with respect to the carrier of from about 0.1:1 to about 2.3:1. The compressible granule is preferably about 10 wt. % to about 70 wt. % fructose, more preferably from about 20 wt. % to about 55 wt. % fructose.

Suitable substantially water insoluble carriers include tricalcium phosphate, dicalcium phosphate anhydrous, magnesium carbonate, and mixtures thereof. A particularly preferred substantially water insoluble carrier is magnesium carbonate due to its ability to carry, or adsorb, relatively large amounts of fructose and its excellent flowability in preparing a composition in accordance with the present invention.

In another aspect of the present invention, a composition useful in tablets as a direct compression excipient is formed by fluidizing a quantity of a substantially water insoluble inorganic salt, spraying a fructose solution onto the fluidized inorganic salt to form compressible granules, and drying the compressible granules to a moisture content of not greater than about 2 wt. %. Preferred particle size of the granules is from about $50\mu$ to about $300\mu$, more preferably from about $100\mu$ to about $200\mu$.

Compositions in accordance with the present invention provide granules with excellent flowability and compressibility properties. These compressible granules may be directly compressed into chewable tablets, or may be admixed with relatively large quantities of a variety of other ingredients, such as vitamins and minerals, and the admixture then directly compressed into tablets. Further, compositions in accordance with the present invention are about as sweet as the sweetest of the presently available direct compression vehicles.

Typical tablets prepared from compositions of the present invention have a friability of not greater than about 1%, and more usually of about 0.3 to about 0.6%.

BRIEF DESCRIPTION OF THE DRAWINGS

In the photomicrographs.

BEST MODE OF CARRYING OUT THE INVENTION

Figure 1:
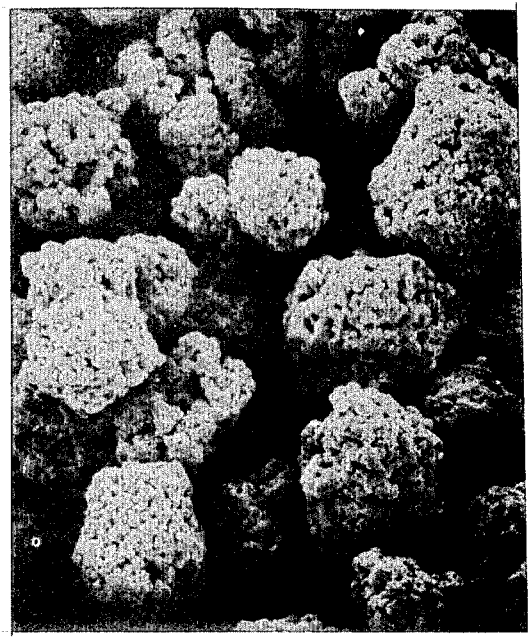
FIG. 1 illustrates a magnesium carbonate embodiment of the present invention at a magnification of 110 times.
Figure 4:
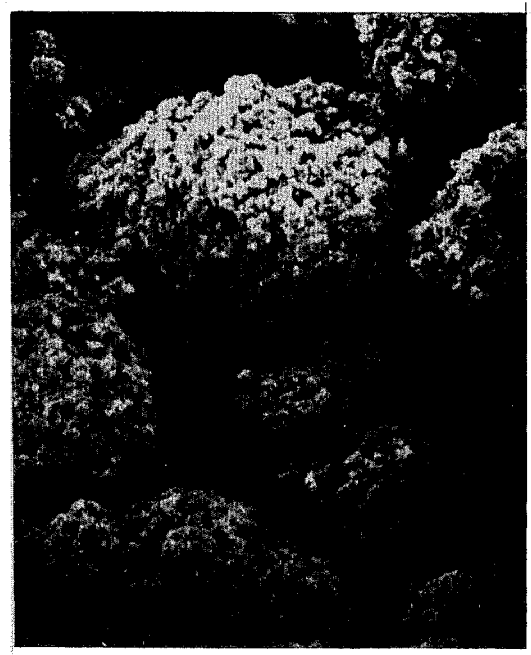
FIG. 4 illustrates a dicalcium phosphate anhydrous embodiment of the present invention at a magnification of 110 times.
Figure 6:
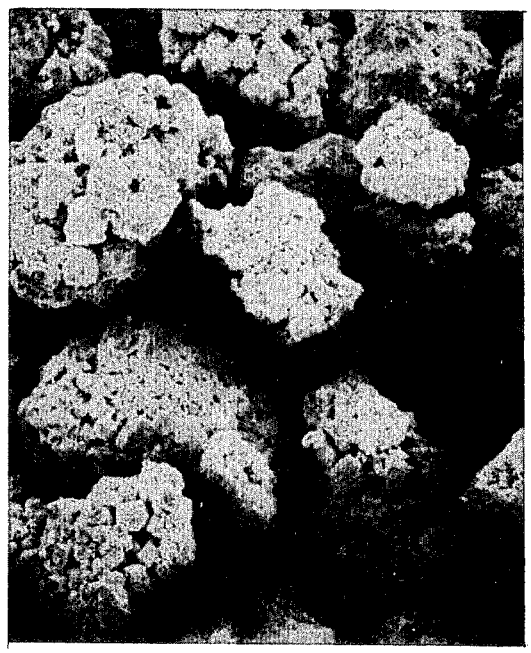

Broadly, the present invention provides a composition in the form of a compressible granule which includes fructose and a substantially water insoluble carrier for the fructose. The compressible granule may vary considerably in particle size, for example may be from about $50\mu$ to about $1000\mu$ in size. The composition of the present invention is particularly useful as a sweet tableting agent for use in tableting with a tableting press. In such use, a plurality of the compressible granules preferably have a particle size of from about 50 microns to about 300 microns, more preferably of from about 100 microns to about 200 microns. FIGS. 1, 4 and 6 depict the surfaces of three preferred embodiments of the present invention.

The inventive composition is preferably formed by the steps comprising fluidizing a quantity of a substantially water insoluble inorganic salt, spraying a solution containing from about 20 to about 80 wt. % of fructose onto the fluidized substantially water insoluble inorganic salt to form the compressible granules, and drying the compressible granules to a moisture content of not greater than about 2 wt. %. The fluidizing and spraying steps may be performed in a fluidized bed granulator system.

The inventive composition and the preferred process by which it is made will now be more fully described.

The compressible granule of the inventive composition is derived from two necessary precursor materials. The one precursor material, fructose, will first be described, followed by a description of the other precursor material, or carrier.

Figure 3:
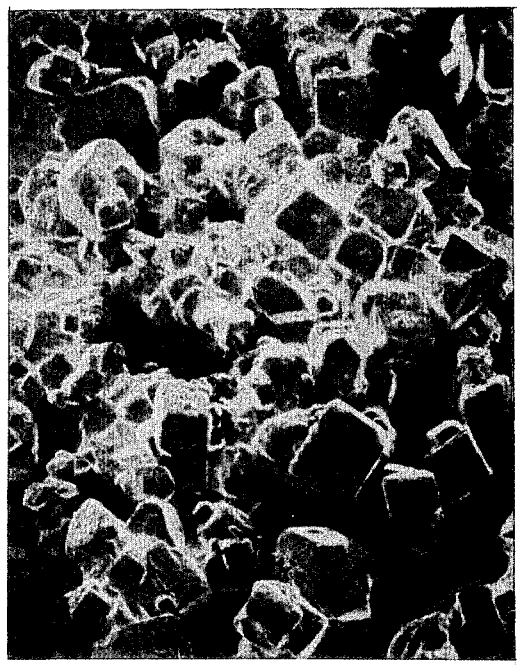
FIG. 3 illustrates precursor fructose, from which the FIG. 1 embodiment was derived, at a magnification of 20 times.

The precursor fructose from which the compressible granule is derived is preferably commercially available, substantially pure, crystalline fructose, which is normally in an anhydrous configuration of β-D fructopyranose. Referring to FIG. 3, anhydrous crystalline, or precursor, fructose is depicted prior to its use in forming a composition in accordance with the present invention. Anhydrous crystalline fructose, such as is depicted by FIG. 3, is insufficiently compressible as to lend itself to tableting under direct compression methods without the presence of an auxiliary, direct compression vehicle.

By contrast, an inventive compressible granule, of which fructose is an integral part, has excellent compressibility and may be directly compressed in a tableting die, or may be readily used with other materials as a direct compression vehicle. It is believed that this surprising difference in compressibility between the anhydrous crystalline fructose precursor and the compressible granule of the present invention is due in major part to a modification of the crystalline structure of fructose in preparing the inventive composition.

Figure 5:
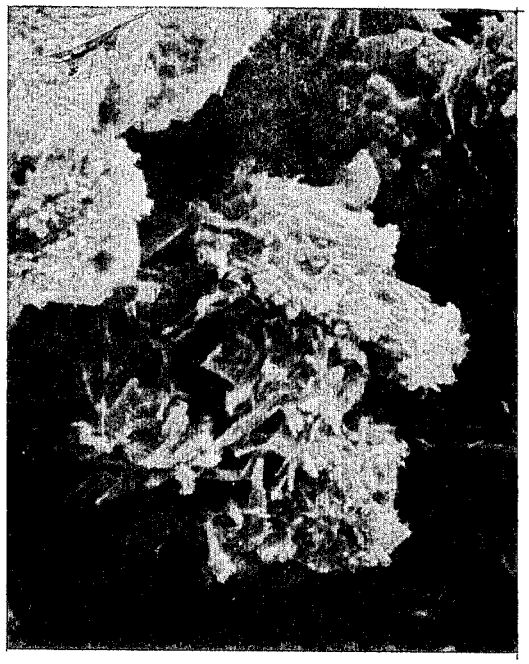
FIG. 5 is a magnification of 2300 times, taken of a surface portion of FIG. 4; and, FIG. 6 is a tricalcium phosphate embodiment in accordance with the present invention at a magnification of 70 times.

Referring to FIG. 5, for example, the needle-like portions depicted therein are tiny crystals of recrystallized fructose on the surface of an inventive compressible granule.

The fructose of the compressible granule is preferably in a weight ratio with respect to the carrier of the compressible granule of from about 0.1:1 to about 2.3:1. Thus, where substantially only fructose and the carrier are present in the compressible granule, the fructose will preferably be about 10 to about 70 wt. % of the compressible granule and the carrier will be the remainder (e.g. about 90 wt. % to about 30 wt. %) of the compressible granule. However, as discussed more fully hereinafter, the compressible granule may also include additional components, if desired, so long as such additional components do not prevent compressibility of the granule and/or flowability thereof.

Precursor materials suitable as carriers of the present invention should be particulate solids, preferably in a particle size of from about 3 to about 50 microns, more preferably about 3 to 20 microns, and are preferably substantially water insoluble. For example, various inorganic salts are suitable precursor materials for the inventive composition. Where the desired use of the inventive composition is as a sweet tableting agent, the precursor material should be edible.

Particularly preferred precursor materials are tricalcium phosphate, dicalcium phosphate anhydrous, magnesium carbonate, and mixtures thereof. These edible, substantially water insoluble inorganic salts are commercially available in particulate, or powdered, form; but, like the precursor anhydrous crystalline fructose, they lack sufficient compressibility for use as direct compression vehicles in tableting. Their presence in prior tableting formulations has been for other, special functions such as glidants, excipients, and the like.

A more preferred range of fructose in the compressible granule is from about 20 wt. % to about 55 wt. %. Where the precursor material for the carrier is magnesium carbonate, tricalcium carbonate, or mixtures thereof, then the most preferred range of fructose is about 35 wt. % to about 55 wt. % of the compressible granule, and where dicalcium phosphate anhydrous is the precursor material then the most preferred range of fructose is from about 20 wt. % to about 25 wt. % of the compressible granule.

Figure 2:
FIG. 2 illustrates precursor magnesium carbonate, from which the FIG. 1 embodiment was derived, at a magnification of 300 times.

FIG. 2 depicts a typical, commercially available quantity of magnesium carbonate having a particle size of about 3 to about 20 microns, which is particularly useful as, and a most preferred, precursor material in forming the inventive composition.

The compressible granule is derived from the precursor fructose and the suitable carrier precursor as an agglutination therebetween with fructose adsorbed on the carrier. More particularly, the compressible granule preferably includes a plurality of carrier particles disposed in a matrix of fructose. For example, FIG. 1 illustrates a plurality of generally spheroidal compressible granules having a particle size of about 100 to about 150 microns.

The FIG. 1 compressible granules will sometimes be referred to as the magnesium carbonate embodiment. An average one granule of the magnesium carbonate embodiment depicted in FIG. 1 is about 50 wt. % magnesium carbonate, about 50 wt. % fructose, and has a moisture content of not greater than about 2 wt. %.

Similarly, FIG. 4 depicts a plurality of compressible granules in accordance with the present invention (sometimes referred to as the dicalcium phosphate anhydrous embodiment) with dicalcium phosphate anhydrous in an amount of about 75 wt. %, fructose of about 25 wt. %, and a moisture content of less than about 2%.

The plurality of compressible granules depicted in FIG. 4 are about 150 to about 200 microns in size.

In like manner, FIG. 6 depicts a plurality of compressible granules (sometimes referred to as the tricalcium phosphate embodiment) of about 100 to about 150 microns in size. The compressible granules therein depicted have about 64 wt. % tricalcium phosphate, about 36 wt. % fructose, and less than about 2 wt. % moisture.

Preparation of the inventive composition, wherein the compressible granule is formed from fructose and a substantially water insoluble carrier for the fructose, will now be exemplified by Examples I-III, below. The magnesium carbonate embodiment prepared in Example I is depicted in FIG. 1. Similarly, the embodiments prepared in Examples II and III are depicted in FIGS. 4 and 6 respectively. Process parameters common to Examples I-II are presented in Table I. The process parameters for Example III are presented in Table II.

EXAMPLE I (Magnesium Carbonate Embodiment)

A Glatt Granulator WSG-15 was charged with 6 kg of Magnesium Carbonate (Heavy-USP Grade). The spray nozzle equipped with a 1.8 mm liquid orifice was positioned at the height of #7 setting. Six and one-half kg of anhydrous crystalline fructose was mixed with 4.5 liters of water at 50° C. in a separate container to form an aqueous solution of fructose.

The Magnesium Carbonate was fluidized and when the outlet air temperature reached 38° C., spraying of the fructose solution, by means of a pulsating pump, commenced. Fluidization was maintained during the spray cycle by adjusting the outlet air flap from an initial setting of 30% to 45% opening. The outlet air temperature during the spray cycle was maintained between 32°-40° C.

Once the fructose solution was depleted, the drying cycle started, during which the inlet air temperature was adjusted between 70°-90° C. to maintain an outlet air temperature between 53° to 55° C. for a duration of 15 minutes. After completion of the drying cycle, the granules were discharged into a polyethylene bag. The granulation was subsequently screened through a #16 mesh, U.S. standard screen, discarding the overs. The resultant granules had a moisture content of about 0.5 wt. %.

EXAMPLE II (Dicalcium Phosphate Anhydrous Embodiment)

A Glatt Granulator WSG 15 was charged with 12 kg. of Dicalcium Phosphate Anhydrous, NF Grade. The spray nozzle equipped with a 2.2 mm liquid orifice was positioned at the height of #5 setting. Four kilograms of anhydrous crystalline fructose were mixed with three liters of water at 50° C. in a separate container.

The Dicalcium Phosphate was fluidized and, when the outlet air temperature reached 35° C., spraying of the fructose solution, by means of a pulsating pump, commenced. Fluidization was maintained during the spray cycle by adjusting the outlet air flap between 30% and 50% opening. The outlet air temperature during the spray cycle was maintained between 30°-38° C.

When all the fructose solution was sprayed, the drying cycle started, during which the inlet air temperature was adjusted between 70°-90° C. to maintain an outlet air temperature between 53° C. to 55° C. for a duration of 15 minutes.

After completion of the drying cycle, the granules were discharged into a polyethylene bag, at which time the granulation was screened through a #25 mesh, U.S. standard screen, discarding the overs. The resultant granules had a moisture content of about 0.5 wt. %.

TABLE I

| | |
|---|---|
| Air Dome Setting | Three complete turns down |
| Inlet Air Temperature | 80° C. |
| Atomization Air | 3½ bars |
| Spray Rate | 240 ml/min. |
| Inlet Air Flap | 100% opening |
| Outlet Air Flap | Adjusted according to maintain a proper level of fluidization during the granulation process, never exceeding a 50% opening. |
| Drying Temperature | (outlet) 55° C. Held for 15 minutes, (inlet) 70-90° C. |
| Shake Time | Approximately twice/minute for a duration of 3-5 sec. |

EXAMPLE III (Tricalcium Phosphate Embodiment)

A Glatt Granulator WSG-15 was charged with 8 kg of Tricalcium Phosphate. The spray nozzle, equipped with a 2.2 mm liquid orifice was positioned at the height of #3 setting. A solution of 3 liters of water at 50° C. was mixed with 4.5 kg. of anhydrous crystalline fructose in a separate container.

The Glatt Container was turned on and immediately the fructose solution was sprayed by means of a pulsating pump. Fluidization was minimal at first, but after spraying 2000 ml of the fructose solution, fluidization increased dramatically. At that time the nozzle height was positioned at setting #5, and the spray cycle continued until the fructose solution was depleted.

The drying cycle commenced and drying of the granulation took place by incrementally increasing the inlet air temperature 5° C. every 3-4 minutes, finally reaching a temperature of 85° C. The granulation was dried to an outlet temperature of 55° C. After completion of the drying cycle, the granules were discharged into a polyethylene bag. The granulation was subsequently screened through a #16 mesh, U.S. standard screen, discarding the overs. The resultant granules had a moisture content of about 1.0 wt. %.

TABLE II

| | |
|---|---|
| Air Dome Setting | Three complete turns down |
| Inlet Air Temperature | 65° C. |
| Atomization Air | 3½ bars |
| Spray Rate | 210 ml/mm |
| Inlet Air Flap | 100% opening |
| Outlet Air Flap | Adjusted according to maintain a proper level of fluidization during the granulation process, never exceeding a 50% opening. |
| Drying Temperature | (outlet) 55° C. (inlet) 70-90° C. |

The inventive composition, or sweet tableting agent, is usefully admixed with other ingredients, such as materials to assist in tablet disintegration, flowing agents to aid in powder flow, lubricants to assist in tablet ejection from the tableting die, flavor oils, and active materials such as vitamins and drugs. Where the inventive compressible granules are admixed with other ingredients, the inventive composition, or sweet tableting agent, will normally function as the sole compression vehicle for such formulations; however, other direct compression vehicles may also be incorporated, if desired.

The inventive sweet tableting agent functions in tableting formulations as a direct compression vehicle which gives at least as good, and frequently better, compressibility than most commercially available direct compression vehicles. Consequently, in many tableting formulations less of the inventive composition will be necessary to provide compression comparable to presently available direct compression vehicles. Thus, thinner tablets, if desired, may be produced.

Examples IV–VII, below, illustrate use of the inventive composition, or sweet tableting agent, in various tablet formulations. Examples IV–VII also include comparative data, further discussed hereinafter.

The compositions of Examples IV–VII were all compressed on a Stokes D-3B press at 475 RPM. Friability was measured for 10 minutes in a Roche Friabilator. Ten tablets were used to measure thickness (by a Mytotoyu Thickness Gauge) and hardness (by a Schleuniger Hardness Tester). Disintegration using six tablets in water at 37° C., was measured in a USP Disintegration Apparatus. By "capping" is meant a lamination of tablet surface.

EXAMPLE IV

| formulation: | of invention (mg/tab) | of Comparison (mg/tab) |
|---|---|---|
| Magnesium Carbonate | — | 269 |
| Fructose | — | 291 |
| Sweet Tableting Agent from Example I | 560 | — |
| Modified Cellulose Gum (disintegrant) | 12 | 12 |
| Silicon Dioxide (flowing agent) | 10 | 10 |
| Calcium Stearate (lubricant) | 18 | 18 |
| | 600 mg. | 600 mg. |

| results: | of invention | of comparison |
|---|---|---|
| Diameter | 7/16" | 7/16" |
| Friability | 0% | capping |
| Thickness | 7.2–7.3mm | — |
| Hardness | 11–19 SCU | — |
| Disintegration | 28 min. | — |

EXAMPLE V

| formulation: | of invention (mg/tab) | of comparison (mg/tab) |
|---|---|---|
| Dicalcium phosphate Anhydrous | — | 495 |
| Fructose | — | 165 |
| Sweet Tableting Agent from Example II | 660 | — |
| Modified Cellulose Gum (disintegrant) | 12 | 12 |
| Silicon Dioxide (flowing agent) | 10 | 10 |
| Calcium Stearate (lubricant) | 18 | 18 |
| | 700 mg. | 700 mg. |

| results: | of invention | of comparison |
|---|---|---|
| Diameter | 7/16" | 7/16" |
| Friability | .3–.4% | capping |
| Thickness | 4.9–5.0mm | — |
| Hardness | 17–20 SCU | — |
| Disintegration | 6 min. | — |

| | of invention (mg/tab) | | | of comparison (mg/tab) | |
|---|---|---|---|---|---|
| formulation: | (a) | (b) | (c) | (d) | (e) |
| Dicalcium Phosphate Dihydrate Unmilled (excipient) | 350 | 400 | 575 | 350 | 400 |
| Potassium Gluconate (mineral) | 160 | 185 | 185 | 160 | 185 |
| Sweet Tableting Agent (Example I) | 150 | — | — | — | — |
| Sweet Tableting Agent (Example II) | — | 175 | — | — | — |
| Fructose, Crystalline | — | — | — | 78 | 43 |
| Magnesium Carbonate, Heavy Powder | — | — | — | 72 | — |
| Dicalcium Phosphate, Anhydrous | — | — | — | — | 132 |
| Modified Cellulose Gum (disintegrant) | 7 | 7 | 7 | 7 | 7 |
| Calcium Stearate (lubricant) | 9 | 8 | 8 | 9 | 8 |
| | 676 | 775 | 775 | 676 | 775 |

| | of invention | | of comparison | | |
|---|---|---|---|---|---|
| results: | (a) | (b) | (c) | (d) | (e) |
| Diameter | 7/16" | 7/16" | 7/16" | 7/16" | 7/16" |
| Friability | .3–.4% | .4–.5% | capping | capping | .9–1% |
| Hardness | 10–13 SCU | 12–15 SCU | 10–14 SCU | - | 10–12 SCU |
| Thickness | 5.4–5.5mm | 5.6–5.8mm | 5.8–5.9mm | — | 5.8–5.9mm |

| | | | | | |
|---|---|---|---|---|---|
| -continued | | | | | |
| Disintegration | 10 min. | 6 min. | — | — | 1 min. |

EXAMPLE VI

| formulation: | of invention (mg/tab) | of comparison (mg/tab) |
|---|---|---|
| Sweet Tableting Agent from Example III | 560 | — |
| Modified Cellulose Gum (disintegrant) | 12 | 12 |
| Silicon Dioxide (flowing agnet) | 10 | 10 |
| Calcium Stearate (lubricant) | 18 | 18 |
| Tricalcium Phosphate | — | 358 |
| Fructose | — | 202 |
| | 600 mg | 560 mg |
| results: | of invention | of comparison |
| Diameter | 7/16" | 7/16" |
| Friability | 0% | capping |
| Thickness | 5.4–5.5 mm | — |
| Hardness | 12–14 SCU | — |
| Disintegration | 15 min. | — |

EXAMPLE VII

| formulation: | of invention (mg/tab) | of comparison (mg/tab) |
|---|---|---|
| Dicalcium Phosphate Dihydrate Unmilled (excipient) | 350 | 350 |
| Potassium Gluconate | 160 | 160 |
| Sweet Tableting Agent (of Example III) | 150 | — |
| Fructose, Crystalline | — | 54 |
| Tricalcium Phosphate | — | 96 |
| Modified Cellulose Gum (disintegrant) | 7 | 7 |
| Calcium Stearate (lubricant) | 9 | 9 |
| | 676 | 676 |
| results | of invention | of comparison |
| Diamter | 7/16" | 7/16" |
| Friablity | .5–.6% | capping |
| Hardness | 11–12 SCU | — |
| Thickness | 5.3–5.4 mm | — |
| Disintegrant | 6 min. | — |

The comparison data from Examples IV–VII demonstrate that fructose and magnesium carbonate, fructose and dicalcium phosphate anhydrous, and fructose and tricalcium phosphate, when used as simply admixed, individual materials lack sufficient compressibility to produce an adequately compressed tablet. However, as illustrated by data of the invention in Examples IV–VII, when fructose is incorporated with magnesium carbonate, dicalcium phosphate anhydrous, or tricalcium phosphate as the inventive sweet tableting agent, a compressed tablet is formed with excellent physical characteristics.

As previously described and illustrated by Examples I–III, the inventive composition, useful in tablets as a sweet tableting agent, is preferably formed by a fluidized bed granulator system. Such preferred formation is by first fluidizing a quantity of the substantially water insoluble inorganic salt. The fluidization may be accomplished by passing a current of warm air upward through a powdered quantity of the substantially water insoluble inorganic salt. Next a solution, normally an aqueous solution, containing from about 20 to about 80 wt. % of fructose, is sprayed onto the fluidized substantially water insoluble inorganic salt. The spraying preferably is wherein the solution is sprayed as atomized droplets.

It is believed that when the atomized droplets of fructose solution come into contact with fluidized particles of the inorganic salt, two or more of the fluidized particles are held together by the atomized solution. That is, the atomized fructose solution forms a liquid bridge between the inorganic salt particles. During the spraying step, it is believed that additional particles of the inorganic salt adhere as additional droplets of the fructose solution continue to be sprayed on the growing granules.

At the conclusion of the spraying step, the compressible granules are dried to a moisture content of not greater than about 2 wt. %, and more preferably to a moisture content of about 0.5 wt. % to about 1 wt. %. It is believed that as drying proceeds, the liquid bridges of fructose solution holding the inorganic salt particles together form solid bridges of recrystallized fructose having a crystalline structure modified with respect to the precursor crystalline fructose. The compressible granules recovered from the drying step are typically rather spongy and fluffy.

The fructose solution which is sprayed may include other soluble components, such as dyes, drugs, and the like if desired, which may thus be incorporated into the resultant compressible granules of the present invention.

INDUSTRIAL APPLICABILITY

A particularly preferred use of the inventive composition, or sweet tableting agent, is as the sole binder and compression vehicle in a vitamin tablet, such as a multiple vitamin B and vitamin C tablet, having a formulation such as follows:

| | mg/tab |
|---|---|
| Sweet tableting agent (of Example III) | 220 |
| Coated Niacinamide (vitamin) | 100 |
| Niacinamide Ascorbate (vitamin) | 80 |
| Coated Thiamine Mononitrate (vitamin) | 25 |
| Coated Riboflavin (vitamin) | 24 |
| Coated Pyridoxine Hydrochloride (vitamin) | 36 |
| d-Calcium Pantothenate (vitamin) | 17 |
| Silicon Dioxide (flowing agent) | 5 |
| Modified Cellulose Gum (disintegrant) | 12 |
| Calcium Stearate (lubricant) | 8 |
| | 527 mg. |

Tablets prepared from the above formulation exhibited a friability of about 0% and took about 14 minutes to disintegrate.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A composition consisting essentially of:
fructose and a substantially water insoluble carrier for the fructose, the fructose and the carrier together forming a compressible granule, the fructose being in a weight ratio with respect to the carrier of from about 0.1:1 to about 2.3:1, the carrier for the fructose being an edible, inorganic salt.

2. The composition as in claim 1 wherein:
the compressible granule includes a plurality of carrier particles disposed in a matrix of fructose.

3. The composition as in claim 1 wherein:
the granule has a moisture content of not greater than about 2 wt. %.

4. The composition as in claim 1 wherein:
the carrier for the fructose is selected from the group consisting of tricalcium phosphate, dicalcium phosphate anhydrous, magnesium carbonate and mixtures thereof.

5. The composition as in claim 2 wherein:
the compressible granule has a particle size of about 100 microns to about 200 microns.

6. The composition as in claim 5 wherein:
the fructose is about 20 wt. % to about 55 wt. % of the compressible granule.

7. A sweet tableting agent comprising:
a plurality of compressible granules having a particle size of from about 50 to about 300 microns, the granules derived from an agglutination between fructose and an edible, substantially water insoluble inorganic salt, an average one granule having a moisture content of not greater than about 2 wt. % and consisting essentially of fructose and the edible, substantially water insoluble salt.

8. The sweet tableting agent as in claim 7 wherein:
the fructose is from about 20 to about 55 wt. % with respect to the average one granule of the plurality of granules.

9. The sweet tableting agent as in claim 7 wherein:
the edible, substantially water insoluble inorganic salt is selected from the group consisting of tricalcium phosphate, dicalcium phosphate anhydrous, magnesium carbonate, and mixtures thereof.

10. A sweet tableting agent formed by the steps comprising:
forming a substantially dry fluidized bed of a substantially water insoluble inorganic salt;
spraying a solution containing from about 20 to about 80 wt. % of fructose onto the fluidized bed of substantially dry water insoluble inorganic salt to form granules; and
drying the granules to a moisture content of not greater than about 2 wt. %, the dried granules being directly compressible.

11. The composition as in claim 10 wherein:
the inorganic salt of the fluidized bed has an particle size of from about 3 to about 50 microns and is selected from the group consisting of tricalcium phosphate, anhydrous calcium phosphate, magnesium carbonate, and mixtures thereof.

12. The composition as in claim 10 wherein:
the fructose solution is sprayed as atomized droplets.

13. The sweet tableting agent as in claim 10 wherein:
the dried granules consist essentially of fructose and inorganic salt.

14. The sweet tableting agent as in claim 13 wherein:
the fructose of the dried granules is crystallized thereon.

15. The sweet tableting agent as in claim 7 wherein:
the fructose of the average one granule is adsorbed thereon.

* * * * *

UNITED STATES PATENT AND TRADEMARK OFFICE
CERTIFICATE OF CORRECTION

PATENT NO. : 4,352,821
DATED : October 5, 1982
INVENTOR(S) : Doran et al.

It is certified that error appears in the above—identified patent and that said Letters Patent is hereby corrected as shown below:

Column 6, line 34, "Container" should be --Granulator--

Signed and Sealed this

Fifteenth Day of February 1983

[SEAL]

Attest:

GERALD J. MOSSINGHOFF

Attesting Officer

Commissioner of Patents and Trademarks